United States Patent [19]

Hirose

[11] Patent Number: 4,722,901
[45] Date of Patent: Feb. 2, 1988

[54] METHOD AND APPARATUS FOR THE ULTRASONIC TREATMENT OF A DILUTE ALCOHOLIC SOLUTION

[76] Inventor: Masanao Hirose, 2-9-93, Kodo, Adachi-ku Tokyo-to, Japan

[21] Appl. No.: 858,925

[22] Filed: May 2, 1986

Related U.S. Application Data

[62] Division of Ser. No. 646,062, Aug. 31, 1984, Pat. No. 4,599,459.

[51] Int. Cl.$^4$ ............................................... C12M 1/00
[52] U.S. Cl. .................................. 435/287; 435/291; 261/DIG. 48; 159/900
[58] Field of Search ............... 435/161, 287, 291, 302, 435/288; 159/900; 203/19, 99, DIG. 13; 261/DIG. 48, DIG. 65, 81; 422/130, 184, 187; 568/471

[56] References Cited

U.S. PATENT DOCUMENTS

| | | | |
|---|---|---|---|
| 2,265,762 | 12/1941 | McKittrick et al. | 261/81 |
| 3,317,405 | 5/1967 | Brown | 159/900 |
| 3,686,077 | 8/1972 | De Koning | 203/99 |
| 4,316,956 | 2/1982 | Lutzen | 435/161 |
| 4,407,954 | 10/1983 | Clyde | 435/288 |

Primary Examiner—Samuel Scott
Assistant Examiner—Noah Kamen
Attorney, Agent, or Firm—Oblon, Fisher, Spivak, McClelland & Maier

[57] ABSTRACT

An apparatus for the ultrasonic treatment of dilute alcoholic solution in which a vibrator member placed in a dilute alcoholic solution is subjected to ultrasonic vibrations to produce cavitation in the solution in such a way that alcohol in the solution is vaporized and collected in a high concentration. The alcohol may be readily converted into a corresponding aldehyde.

7 Claims, 1 Drawing Figure

METHOD AND APPARATUS FOR THE ULTRASONIC TREATMENT OF A DILUTE ALCOHOLIC SOLUTION

This is a division of application Ser. No. 646,062, filed Aug. 31, 1984 now U.S. Pat. No. 4,599,459.

BACKGROUND OF THE INVENTION

1. Field of the Invention

This invention relates to a method for the ultrasonic treatment of a dilute alcoholic solution in which the alcohol is vaporized from the dilute alcoholic solution.

2. Description of the Prior Art

Ultrasonic vibrations have been heretofore used to oscillate vibrators in water, with the result that cavitation is produced thereby generating steam. Alternatively, ultrasonic vibrations are utilized to be acted on liquors in order to facilitate removal of froth from beer or aging of whisky. However, ultrasonic vibrations have never been utilized for vaporization of alcohol without causing cavitation.

In the fermentation of alcohol, when a concentration of alcohol reaches a certain level, e.g. about 12%, the alcohol productivity of yeast fungii is suppressed. In recent years, alcohol-resistant fungii have been discovered but even with such fungii, the alcohol productivity is suppressed when the alcohol concentration exceeds 15%. About 10% to 20% of carbohydrates added to a fermentation mother liquor remains unfermented. Especially, when starting starchy materials are saccharified with aspergilli and are subsequently subjected to alcoholic fermentation by means of yeast fungii as with Sake, about 50% of the added starchy materials is left as sake lees in the form of dextrin, cellulose and starchy materials. This arises problems from the standpoint of saving resources and preventing ecological pollution. Moreover, it is generally accepted that for the production of alcoholic liquors having high concentrations by distillation of the liquors obtained by filtration of the fermentation liquor, about 7.5 liters of petroleum as fuel per 10 liters of the alcohol product is required. Additionally, a cooling energy which is used to cool and condense once vaporized alcohol is not negligible. It is known that production of alcohol having a high concentration requires petroleum in the same amount as the alcohol.

It is also known that for the production of aldehydes such as formaldehyde, acetoaldehyde and the like, organic and inorganic mercury compounds which involve environmental pollution problems are used.

SUMMARY OF THE INVENTION

It is an object of the present invention to provide a method for the ultrasonic treatment of dilute alcoholic solutions which overcomes the drawbacks of the prior art and in which an alcohol solution having a high concentration can be produced from a dilute alcoholic solution by vaporizing the alcohol therefrom by the use of only a slight energy.

It is another object of the invention to provide a method for the ultrasonic treatment of dilute alcoholic solutions which enables one to carry out continuous alcoholic fermentation without lowering a concentration of starting materials in the fermentation system.

It is a further object of the invention to provide a method for the ultrasonic treatment of dilute alcoholic solutions from which aldehydes can be produced in a very simple manner without use of any organic or inorganic mercury compounds, thus not involving any environmental pollution problems.

The above objects can be achieved, according to the invention, by a method for the ultrasonic treatment of a dilute alcoholic solution which comprises placing a vibrator member in a dilute alcoholic solution, and subjecting the vibrator member in the dilute alcoholic solution to ultrasonic vibration to cause cavitation whereby the alcohol in the solution is vaporized.

BRIEF DESCRIPTION OF THE DRAWING

A sole FIGURE is an illustrative view of an apparatus for carrying out the method of the invention.

DETAILED DESCRIPTION OF THE INVENTION

Figure 1:
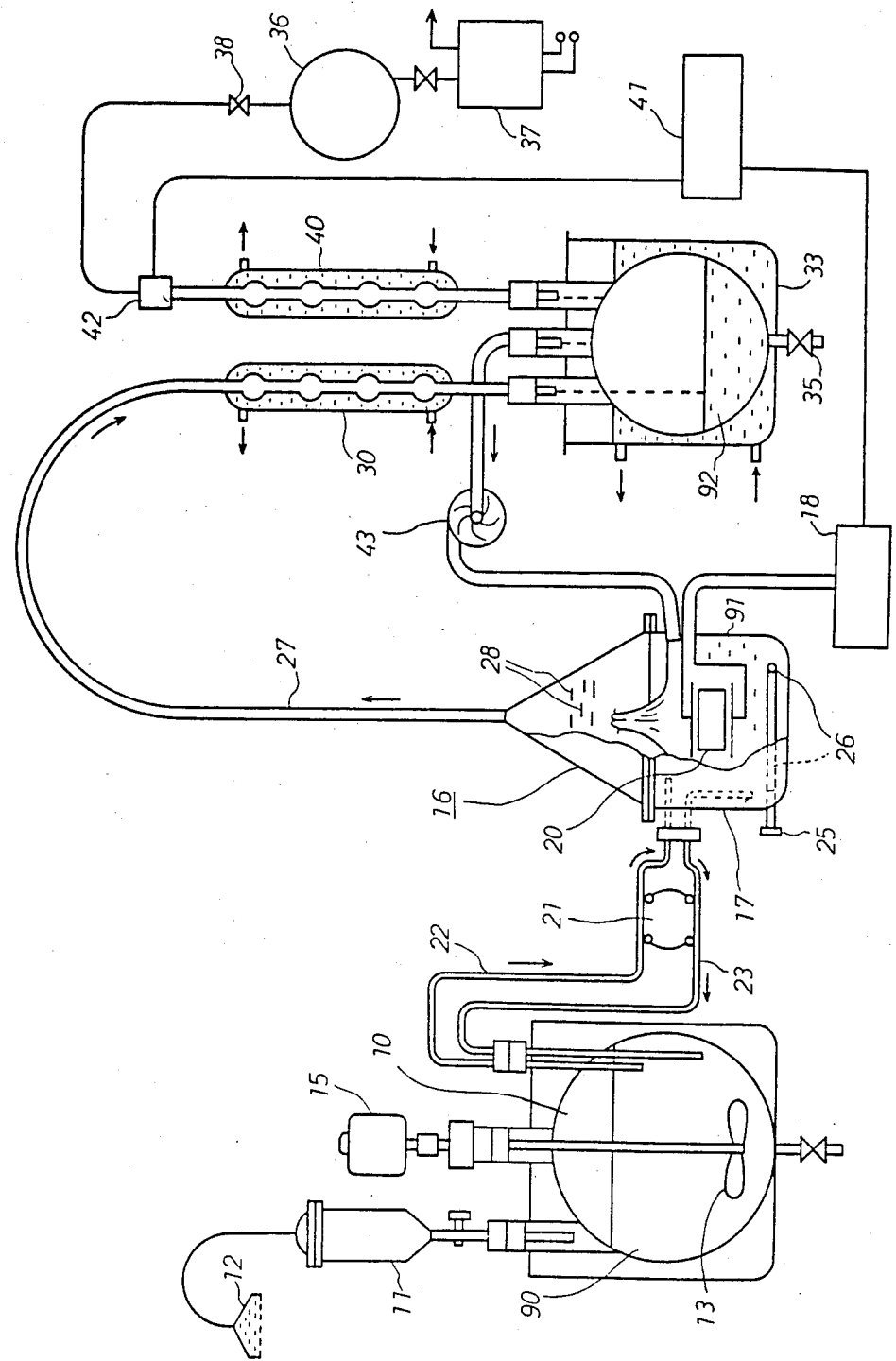

Reference is now made to the accompanying drawing which illustrates an embodiment according to the invention. In the FIGURE, indicated at 10 is a fermenter, at 11 is a tank for starting material from which a starting material is fed into the fermenter, at 12 is microfilter which is associated with the tank 11 and serves to prevent various bacteria from entering, at 13 is a agitator blade for agitating a mother liquor 90 being fermented in the fermenter 10, and at 15 is a motor for driving the agitator blade. Around the fermenter 10 are provided a heater and a cooling water circulator (both not shown) so that the temperature of the content is kept at a given temperature of, for example, about 30° C.

Indicated at 16 is an ultrasonic processor having a container 17 which is in the form of a dish at the lower portion thereof and in the form of an inverted cone at the upper portion and is made, for example, of stainless steel. The processor 16 further includes a vibrator member 20 which is ultrasonically vibrated on reception of a signal current from an ultrasonic wave generator 18. Moreover, the processor 16 is to arranged that the mother liquor 90 in the fermenter 10 is circulated, as a dilute alcoholic solution 91, by means of a circulation pump 21 through pipes 22, 23. Indicated at 25 is a connection port through which an inert gas is fed. The connection port 25 is connected to a bomb (not shown) of an inert gas such as carbon dioxide, nitrogen, helium, hydrogen or the like and the gas is discharged from an inlet port 26 placed in the ultrasonic processor 16, thereby forming an inert gas atmosphere. Of these gases, carbon dioxide is preferred.

In general, the ultrasonic processor 16 may not be directly connected to the fermenter 10. The dilute alcoholic solution 91 accomodated in the fermenter may be methyl alcohol, ethyl alcohol, propyl alcohol, butyl alcohol or the like. With the apparatus shown in the figure, the alcohol-fermented mother liquor, a supernatant liquid of the mother liquor, or a filtrate obtained by filtration of the mother liquor may be fed to the processor 16. The vibrator member 20 may be a quartz vibrator, a barium titanate ceramic vibrator, a nickel ferrite vibrator, a magnetostrictive metal vibrator, or a member provided in the container 17 and integrally combined with the above-mentioned vibrators located at the outside of the container 17. The vibrator member 20 is oscillated by means of the ultrasonic wave generator of $10^4$ to $10^7$ Hz.

Cavitation is produced by ultrasonically vibrating the vibrator member 20 very slightly under conditions where the pressure in the ultrasonic processor 16 is initially, transiently reduced, so that the alcohol in the solution 91 is vaporized. Once the cavitation takes place, so-called intoxication is produced and thus even though the inner pressure increases due to the vaporization of the alcohol, the cavitation continues. Upon occurrence of the cavitation, the alcohol is vaporized and the solution 91 moves upwards at the above portion of the vibrator member 20 as shown. The vaporized alcohol is fed through a pipe 27 connected with the container 17 at the upper end thereof. Indicated at 28 are a plurality of bumping-preventive perforated plates which are vertically spaced from one another in such a way that the holes of the respective plates are not superposed, by which the bumping of the solution 91 in which the solution jumps as a liquid column at the upper portion of the container 17 is properly prevented. The electric power required for the vaporization of the dilute alcoholic solution 91 by cavitation caused by ultrasonic vibrations is mucn smaller than the case where the vaporization is by heating. If large ultrasonic vibrations are given to the vibrator member 20, even water may be vaporized by the resulting cavitation. On the other hand, slight ultrasonic vibrations lead to vaporization of the alcohol alone.

Indicated at 30 is solid matter-adsorption and condensation column in which the vaporized alcohol fed through the pipe 27 is adsorbed and condensed. In the column are filled powder moldings such as carbon black or active carbon, fluorine resin powder moldings, fluorinated graphite powder moldings, fluorinated graphite fibers and the like. The column is arranged to be cooled by means of cooling water, but an arrangement may be used in which no cooling water is used. Indicated at 33 is a reservoir for receiving a liquefied, highly concentrated alcohol 92 passed through the solid matter-adsorption and condensation column 30. The reservoir is provided with a cooling means and cooled. At 35 is a discharge port from which the alcohol from the reservoir 33 is discharged. Indicated at 36 is a vacuum tank evacuated through a vacuum pump 37. The tank 36 is connected to the reservoir 33 and used to reduce the pressure within the ultrasonic processor 16. In general, when the cavitation is kept continued, a valve 38 is closed. If necessary, the vacuum pump 37 may be continuedly operated in order to reduce the pressure within the ultrasonic processor 16. Indicated at 40 is another solid matter-adsorption and condensation column provided between the vacuum pump 36 and the reservoir 33 and having the same construction as the column 30. This column serves to liquefy the alcohol vaporizing in the reservoir 33 at the time of vacuum suction, thus preventing the vaporized alcohol from entering the vacuum tank 36, followed by returning to the reservoir 33 as drain. Indicated at 41 is a gas chromatography which is automatically controlled by a sensor provided at the upper portion of the column 42. From the information of the sensor are determined an amount and a quality of the gas. If, for example, the vaporized alcohol is large in amounts, the output level of the ultrasonic generator 18 can be lowered. Indicated at 43 is a blower for circulating the inert gas and the alcohol vapor within the reservoir 33 to the ultrasonic processor 16. After the inert gas has been once fed to the ultrasonic processor 16, the blower may stop further feed of the inert gas and serves to liquefy the vaporized alcohol. The inert gas atmosphere is necessary in order to prevent troubles such as formation of aldehydes, explosion and deflagration by oxidation reaction of the vaporized alcohol with gas phase oxygen or oxygen dissolved in the solution 91.

It has been found that if no inert gas atmosphere is present in the ultrasonic processor 16, the alcohol vaporized by the cavitation is oxidized with gaseous oxygen and oxygen dissolved in the solution 91 into aldehydes. However, if the solution 91 which is free of dissolved oxygen is fed, it is possible to produce alcohol alone.

In the practice of the invention, if the vibrator member 20 is ultrasonically vibrated within the ultrasonic processor 16 to produce cavitation while feeding oxygen in a properly controlled concentration such as by adding carbon dioxide to compressed air, for example, from the connection port 25 to have a low oxygen concentration, the vaporized alcohol is oxidized. The oxidation is pronouncedly facilitated by the cavitation with ready formation of aldehydes. The aldehydes are accomodated in the reservoir 33. In this connection, a solid catalyst may be provided near the bumping-preventive plates 28 in the ultrasonic processor 16 for complete conversion into aldehydes. When using methyl alcohol, ethyl alcohol, propyl alcohol and butyl alcohol as the dilute alcohol solution 91, there are, respectively, obtained formaldehyde, acetoaldehyde, propylaldehyde, and butyladlehyde.

As described above, in the practice of the invention, the vibrator member 20 which is placed in the dilute alcoholic solution 91 is ultrasonically vibrated to produce cavitation, by which the alcohol is vaporized. The alcohol can be vaporized at higher efficiencies than the case where the solution 91 is directly heated for vaporization, thus making it possible to save the energy consumption.

Moreover, because no distillation under heating conditions is carried out, koji and yeast fungii surviving in the dilute alcoholic solution 91 are not killed or enzyme is not decomposed. Accordingly, where the alcoholic solution 91 is circulated from the fermenter 10 toward the ultrasonic processor 16, unfermented carbohydrates can be completely converted into alcohol. In addition, to the single fermenter 10 is appropriately added the starting material consisting of a thermally sterilized thick mother liquor from the tank 11 in order not to lower the concentration of the starting material, thereby enabling continuous fermentation of alcohol.

When aldehydes are produced in accordance with the present invention, no organic or inorganic mercury compounds are necessary and thus they can be prepared very simply without involving any problems of environmental pollution.

The present invention is more particularly described by way of examples.

EXAMPLE 1

A Langevin-type quartz vibrator (1.7 MHz, input power 20 W) was used and acted on 300 ml of a 10% ethyl alcohol solution. In an atmosphere of carbon dioxide, the initial pressure in the ultrasonic processor was transiently reduced to 700 mmHg to produce cavitation, causing alcohol vapor to be gushed for about 3 minutes. The vapor was introduced into the solid matter-adsorption and condensation column, thereby obtain about 25 ml of a 87% ethyl alcohol solution

EXAMPLE 2

Using the apparatus shown in the figure, 200 liters of a fermentation mother liquor of 15% theriac to which yeast fungii was added was placed in the fermenter 10 and fermented for 6 hours. Thereafter, the circulation pump 21 was operated to introduce the mother liquor into the ultrasonic processor 16. By the fermentation, the gas phase in the container 17 was a carbon dioxide atmosphere but in order to ensure safety and prevent oxidation of vaporized alcohol, a small amount of carbon dioxide was added. Initially, the vacuum pump 37 was operated so that the pressure of the vacuum tank 36 was reduced. Simultaneously with the operation of the ultrasonic processor 16, the container 17 was reduced in pressure. Ultrasonic vibrations of 20 KHz with an input power of 500 W (maximum output of about 200 W) were used. Under these conditions, the ultrasonic processor 16 started to be operated and cavitation was thus produced, followed by stationary operation. For initial one hour, 8 liters of 85% ethyl alcohol was obtained and a continuous operation of 10 hours resulted in 40 liters of ethyl alcohol.

EXAMPLE 3

A Langevin-type quartz vibrator (1.7 MHz, input power 50 W) was used to produce cavitation in 500 ml of 10% ethyl alcohol solution. As a result, 40 ml of 78% acetoaldehyde solution was obtained in the reservoir 5 minutes after commencement of ultrasonic vibrations.

What is claimed is:

1. An apparatus for the ultrasonic treatment of a dilute solution of a lower aliphatic alcohol, said apparatus comprising:
    a means operable for contacting a solution of lower aliphatic alcohol with a means for generating ultrasounds, wherein the said means for generating ultrasounds comprises a vibrator member operable for contacting a dilute alcoholic solution whereby a portion of the said solution is vaporized;
    a means for detecting the quantity and quality of a part of the said portion being vaporized, said means for detecting controlling said means for generating ultrasounds; and
    a means for condensing and liquefying the vaporized portion.

2. The apparatus of claim 1, wherein the said apparatus comprises a fermentation means for the production of said dilute solution of a lower aliphatic alcohol, said fermentation means being in communication with said apparatus.

3. The apparatus of claim 1, said apparatus comprising a means operable for circulating a dilute solution of a lower aliphatic alcohol from the said fermentation means to the said contacting means.

4. The apparatus of claim 1, wherein the ultrasounds are produced by a vibrator member vibrating within a frequency range of $10^4$ to $10^7$ Hz.

5. The apparatus of claim 4, wherein the vibrator member comprises one of a quartz vibrator, a barrium titanate ceramic vibrator, a nickel ferrite vibrator, or a magnetostrictive metal vibrator.

6. The apparatus of claim 2, wherein said fermentation means is operable to produce a lower aliphatic alcohol which is at least one member selected from the group consisting of methyl alcohol, ethyl alcohol, propyl alcohol, and butyl alcohol.

7. An apparatus for the ultrasonic treatment of a dilute solution of a lower aliphatic alcohol, said apparatus comprising:
    a means operable for contacting a solution of lower aliphatic alcohol with a means for generating ultrasounds, wherein the said means for generating ultrasounds comprises a vibrator member operable for contacting the dilute alcoholic solution whereby a portion of the said solution is vaporized;
    a first solid-matter-adsorption and condensation column for absorbing, condensating and liquefying the vaporized lower aliphatic alcohol;
    a reservoir for receiving the liquefied alcohol fed through the matter-adsorption and condensation column;
    a vacuum tank in communication with said apparatus and a vacuum pump in communication with said vacuum tank and operable to evacuate said vacuum tank;
    a second solid-matter-adsorption and condensation column provided between said reservoir and said vacuum pump;
    a means for detecting the quality and quantity of vaporized lower aliphatic alcohol in said second solid-matter-adsorption and condensation column;
    a means for feeding an electric current to said vibrator member, said means feeding the electrical current in accordance with the quantity of vaporized lower aliphatic alcohol detected by the gas detecting means; and
    a blower for recyclying a gas, in communication with said apparatus.

* * * * *